United States Patent
Iwaki

(10) Patent No.: US 11,176,665 B2
(45) Date of Patent: Nov. 16, 2021

(54) ENDOSCOPIC IMAGE PROCESSING DEVICE AND ENDOSCOPIC IMAGE PROCESSING METHOD

(71) Applicant: OLYMPUS CORPORATION, Hachioji (JP)

(72) Inventor: Hidekazu Iwaki, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 138 days.

(21) Appl. No.: 16/661,005

(22) Filed: Oct. 23, 2019

(65) Prior Publication Data
US 2020/0058124 A1    Feb. 20, 2020

Related U.S. Application Data

(63) Continuation of application No. PCT/JP2017/016173, filed on Apr. 24, 2017.

(51) Int. Cl.
| | | |
|---|---|---|
| G06K 9/00 | (2006.01) | |
| G06T 7/00 | (2017.01) | |
| A61B 1/00 | (2006.01) | |

(52) U.S. Cl.
CPC ........ G06T 7/0012 (2013.01); A61B 1/00009 (2013.01); A61B 1/00045 (2013.01); *G06T 2207/10068* (2013.01)

(58) Field of Classification Search
CPC . A61B 1/00009; A61B 1/00045; A61B 1/045; G06T 2207/10068; G06T 7/0012
See application file for complete search history.

(56) References Cited

U.S. PATENT DOCUMENTS

| | | | | |
|---|---|---|---|---|
| 2011/0254937 A1* | 10/2011 | Yoshino | ............... | A61B 1/0638 348/65 |
| 2014/0049626 A1* | 2/2014 | Ishihara | ................. | G01N 21/64 348/68 |

(Continued)

FOREIGN PATENT DOCUMENTS

| | | |
|---|---|---|
| EP | 3141178 A1 | 3/2017 |
| JP | 2011255006 A | 12/2011 |
| WO | 2016084504 A1 | 6/2016 |

OTHER PUBLICATIONS

International Search Report (ISR) dated Jul. 18, 2017 (and English translation thereof) issued in International Application No. PCT/JP2017/016173.

(Continued)

*Primary Examiner* — Tom Y Lu
(74) *Attorney, Agent, or Firm* — Holtz, Holtz & Volek PC

(57) ABSTRACT

An endoscopic image processing device includes one or more processors. The processors perform: detecting a region of interest for an observation image, the observation image being obtained by picking up an image of an object and being sequentially input to the processors, judging whether detection of the region of interest continues or not to acquire a judgment result, emphasizing with adding visual information for emphasizing a position of the region of interest to the observation image during a period during which the region of interest is detected. The processors cause an appearance of the visual information added to the observation image to differ between a case where the detection of the region of interest continues for a predetermined time period or more and a case where the detection of the region of interest discontinues in a time period shorter than the predetermined time period, based on the judgment result.

7 Claims, 6 Drawing Sheets

(56) References Cited

U.S. PATENT DOCUMENTS

| | | |
|---|---|---|
| 2017/0086659 A1 | 3/2017 | Uchiyama et al. |
| 2018/0249900 A1* | 9/2018 | Imaizumi ............ A61B 1/00009 |
| 2019/0239718 A1* | 8/2019 | Iwaki ....................... A61B 1/05 |

OTHER PUBLICATIONS

Written Opinion of the International Searching Authority dated Jul. 18, 2017 issued in International Application No. PCT/JP2017/016173.

* cited by examiner

ENDOSCOPIC IMAGE PROCESSING DEVICE AND ENDOSCOPIC IMAGE PROCESSING METHOD

CROSS REFERENCE TO RELATED APPLICATION

This application is a continuation application of PCT/JP2017/016173 filed on Apr. 24, 2017, the entire contents of which are incorporated herein by this reference.

BACKGROUND OF THE INVENTION

1. Field of the Invention

The present invention relates to an endoscopic image processing device and an endoscopic image processing method.

2. Description of the Related Art

Conventionally, a surgeon has judged presence/absence of a lesion and the like by viewing an observation image with an endoscope apparatus. In order to prevent a surgeon from overlooking a lesion at the time of viewing an observation image, an endoscope apparatus in which an alert image is added to a region of interest, which has been detected by image processing, to display an observation image is proposed, for example, as shown in Japanese Patent Application Laid-Open Publication No. 2011-255006. Japanese Patent Application Laid-Open Publication No. 2011-255006 also discloses a configuration in which, when an elapsed time period during which the region of interest is continuously detected exceeds a predetermined threshold, the alert image corresponding to the region of interest is hidden.

SUMMARY OF THE INVENTION

An endoscopic image processing device of an aspect of the present invention includes one or more processors. The processors are configured to perform: detecting a region of interest for an observation image, the observation image being obtained by picking up an image of an object and being sequentially input to the processors, judging whether detection of the region of interest continues or not to acquire a judgment result, and emphasizing with adding visual information for emphasizing a position of the region of interest to the observation image during a period during which the region of interest is detected. The processors cause an appearance of the visual information added to the observation image to differ between a case where the detection of the region of interest continues for a predetermined time period or more and a case where the detection of the region of interest discontinues in a time period shorter than the predetermined time period, based on the judgment result.

An endoscopic image processing method of an aspect of the present invention includes: performing, detecting a region of interest for an observation image, the observation image being obtained by picking up an image of an object and being sequentially input to the processors, judging whether detection of the region of interest continues or not to acquire a judgment result, emphasizing with adding visual information for emphasizing a position of the region of interest to the observation image during a period during which the region of interest is detected, and causing an appearance of the visual information added to the observation image to differ between a case where the detection of the region of interest continues for a predetermined time period or more and a case where the detection of the region of interest discontinues in a time period shorter than the predetermined time period, based on the judgment result.

DETAILED DESCRIPTION OF THE PREFERRED EMBODIMENT(S)

Figure 1:
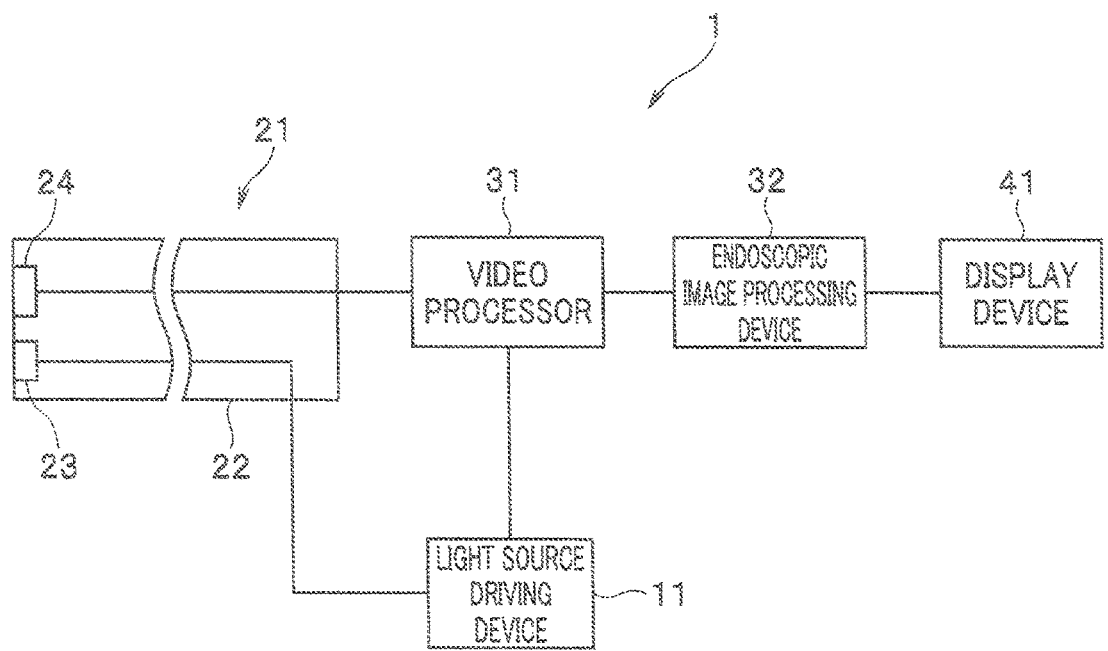
FIG. 1 is a diagram showing a configuration of a main part of an endoscope system including an endoscopic image processing device according to an embodiment.

As shown in FIG. 1, an endoscope system 1 is configured including a light source driving device 11, an endoscope 21, a video processor 31, an endoscopic image processing device 32 and a display device 41. FIG. 1 is a diagram showing a configuration of a main part of an endoscope system including an endoscopic image processing device according to an embodiment.

The light source driving device 11 is configured, for example, being provided with a drive circuit. The light source driving device 11 is connected to the endoscope 21 and the video processor 31. The light source driving device 11 is configured to generate a light source driving signal for causing a light source portion 23 of the endoscope 21 to be driven, based on a light source control signal from the video processor 31, and output the generated light source driving signal to the endoscope 21.

The endoscope 21 is connected to the light source driving device 11 and the video processor 31. The endoscope 21 is configured having an elongated insertion portion 22 that is insertable into an examinee's body cavity. A distal end portion of the insertion portion 22 is provided with the light source portion 23 and an image pickup portion 24.

The light source portion 23 is configured being provided with a light-emitting element, for example, like a white LED. Further, the light source portion 23 is configured to generate illumination light by emitting light in response to the light source driving signal outputted from the light source driving device 11 and radiate the generated illumination light to an object such as living tissue.

The image pickup portion 24 is configured including an image sensor, for example, like a color CCD or a color CMOS. The image pickup portion 24 is configured to perform an operation corresponding to an image pickup control signal outputted from the video processor 31. Further, the image pickup portion 24 is configured to receive reflected light from an object illuminated by illumination light from the light source portion 23, pick up an image of the received reflected light to generate an image pickup signal, and output the generated image pickup signal to the video processor 31.

The video processor 31 is connected to the light source driving device 11 and the endoscope 21. The video processor 31 is configured to generate a light source control signal for controlling a light emission state of the light source portion 23 and output the light source control signal to the light source driving device 11. Further, the video processor 31 is configured to generate an image pickup control signal for controlling an image pickup operation of the image pickup portion 24 and output the image pickup control signal. Further, the video processor 31 is configured to generate an observation image G1 of an object by performing predetermined processing for an image pickup signal outputted from the endoscope 21, and sequentially output frames of the generated observation image G1 to the endoscopic image processing device 32, one frame at a time.

Figure 2:
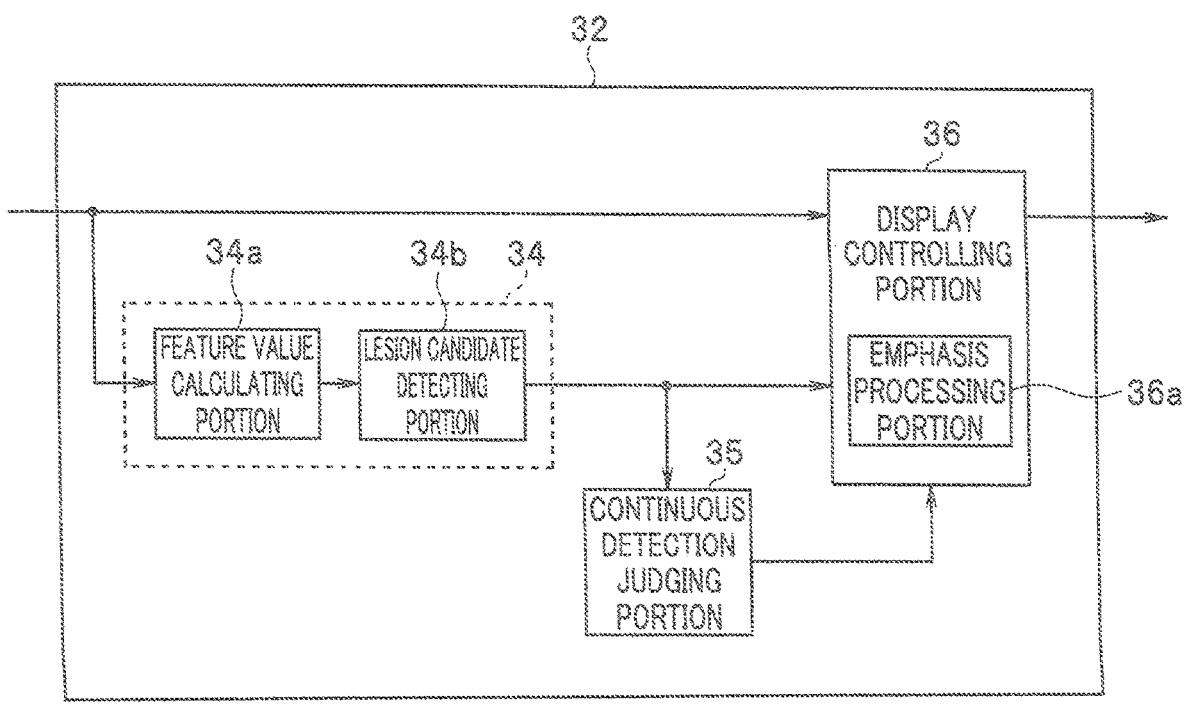
FIG. 2 is a block diagram for illustrating an example of a specific configuration of the endoscopic image processing device according to the embodiment.

The endoscopic image processing device 32 is configured to perform an operation for generating a display image based on the observation image G1 outputted from the video processor 31 and causing the generated display image to be displayed on the display device 41. As shown in FIG. 2, the endoscopic image processing device 32 is configured including a region of interest detecting portion 34, a continuous detection judging portion 35 and a display controlling portion 36. Note that, according to the present embodiment, for example, each portion of the endoscopic image processing device 32 may be configured as an individual electronic circuit or a circuit block in an integrated circuit such as an FPGA (field programmable gate array). Further, according to the present embodiment, for example, at least a part of the endoscopic image processing device 32 may be configured with a CPU. FIG. 2 is a block diagram for illustrating an example of a specific configuration of the endoscopic image processing device according to the embodiment.

The region of interest detecting portion 34 is configured to calculate a predetermined feature value about the observation image G1 sequentially outputted from the video processor 31 and furthermore detect a lesion candidate area L, which is a region of interest included in the observation image G1, based on the calculated predetermined feature value. In other words, the region of interest detecting portion 34 is configured to, when the plurality of frames of the observation image G1 obtained by picking up an image of an object by the endoscope 21 are sequentially inputted, perform processing for detecting the lesion candidate area L for each of the plurality of frames of the observation image G1. As shown in FIG. 2, the region of interest detecting portion 34 is configured including a feature value calculating portion 34a and a lesion candidate detecting portion 34b.

The feature value calculating portion 34a is configured to calculate the predetermined feature value of the observation image G1 sequentially outputted from the video processor 31 and output the calculated predetermined feature value to the lesion candidate detecting portion 34b.

More specifically, the feature value calculating portion 34a calculates, for example, an inclination value which is a value indicating an amount of change in brightness or an amount of change in density between respective pixels in one small area among a plurality of small areas obtained by dividing the observation image G1 into areas of a predetermined size and respective pixels in a small area next to the one small area, as a feature value for each of the plurality of small areas. Note that the feature value calculating portion 34a may calculate a value different from the inclination value described above as the feature value as far as a value capable of quantitatively evaluating the observation image G1 is calculated.

The lesion candidate detecting portion 34b is configured including a nonvolatile memory (not shown) such as ROM in which one or more pieces of polyp model information are stored in advance.

More specifically, each of the pieces of polyp model information stored in the memory of the lesion candidate detecting portion 34b is configured, for example, being provided with a feature value obtained by quantifying common points and/or similar points among a plurality polyp images.

The lesion candidate detecting portion 34b is configured to detect the lesion candidate area L based on the predetermined feature value outputted from the feature value calculating portion 34a and the plurality of pieces of polyp model information read from the memory, acquire lesion candidate information IL, which is information showing the detected lesion candidate area L, and output the acquired lesion candidate information IL to each of the continuous detection judging portion 35 and the display controlling portion 36.

More specifically, for example, if a feature value of one small area outputted from the feature value calculating portion 34a corresponds to at least one feature value included in the plurality of pieces of polyp model information read from the memory, the lesion candidate detecting portion 34b detects the one small area as the lesion candidate area L. Further, the lesion candidate detecting portion 34b acquires the lesion candidate information IL including position information and size information about the lesion candidate area L detected by the method described above, and outputs the acquired lesion candidate information IL to each of the continuous detection judging portion 35 and the display controlling portion 36.

Note that the position information about the lesion candidate area L is information showing a position of the lesion candidate area L in the observation image G1 and is acquired, for example, as a pixel position of the lesion candidate area L existing in the observation image G1. The size information about the lesion candidate area L is information showing a size of the lesion candidate area L in the observation image G1 and is acquired, for example, as the number of pixels of the lesion candidate area L existing in the observation image G1.

The region of interest detecting portion 34 may not be configured including the feature value calculating portion 34a and the lesion candidate detecting portion 34b as far as the region of interest detecting portion 34 performs processing for detecting the lesion candidate area L from the observation image G1. More specifically, the region of interest detecting portion 34 may be configured to detect the lesion candidate area L from the observation image G1, for example, by performing processing for applying an image identifier that has acquired beforehand a function of capable of identifying a polyp image by a learning method such as deep learning, to the observation image G1.

The continuous detection judging portion 35 is configured including a volatile memory (not shown) such as RAM capable of storing at least lesion candidate information IL one frame before, among respective pieces of lesion candidate information IL outputted from the lesion candidate detecting portion 34b.

The continuous detection judging portion 35 is configured to, for example, detect whether a first lesion candidate area shown by first lesion candidate information and a second lesion candidate area shown by second lesion candidate information are the same lesion candidate area L or not based on the first lesion candidate information outputted from the lesion candidate detecting portion 34b and the second lesion candidate information stored in the memory one frame before the first lesion candidate information. The continuous detection judging portion 35 is configured to, if it can be detected that the first and second lesion candidate areas described above are the same lesion candidate area L, acquire a judgment result that detection of the lesion candidate area L in the observation image G1 continues and output the judgment result to the display controlling portion 36. The continuous detection judging portion 35 is configured to, if it cannot be detected that the first and second lesion candidate areas described above are the same lesion candidate area L, acquire a judgment result that detection of the lesion candidate area L in the observation image G1 has discontinued and output the judgment result to the display controlling portion 36. In other words, the continuous detection judging portion 35 is configured to judge whether detection of the lesion candidate area L by the region of interest detecting portion 34 continues or not.

The display controlling portion 36 is configured including a volatile memory (not shown) such as RAM capable of storing at least lesion candidate information IL one frame before, among respective pieces of lesion candidate information IL outputted from the lesion candidate detecting portion 34b. Further, the display controlling portion 36 is configured to, when lesion candidate information IL is inputted from the lesion candidate detecting portion 34b, measure a continuous detection time period TL, which is an elapsed time period after detection of the lesion candidate area L in the observation image G1 is started, based on the judgment result outputted from the continuous detection judging portion 35. Further, the display controlling portion 36 is configured to perform processing for generating a display image using the observation image G1 sequentially outputted from the video processor 31 and perform processing for causing the generated display image to be displayed on a display screen of the display device 41. The display controlling portion 36 is configured being provided with an emphasis processing portion 36a configured to perform emphasis processing for emphasizing the lesion candidate area L existing in the observation image G1. Note that the display controlling portion 36 may cause the display image to be displayed in an area other than the display screen of the display device 41 or on a display device other than the display device 41.

The emphasis processing portion 36a is configured to, during a period during which the continuous detection time period TL is measured, that is, a period during which the lesion candidate area L is detected by the region of interest detecting portion 34, perform emphasis processing for adding a marker image G2, which is visual information for emphasizing a position of the lesion candidate area L, to the observation image G1.

More specifically, the emphasis processing portion 36a is configured to, at a timing when the continuous detection time period TL reaches a time period TM, start the emphasis processing by, based on lesion candidate information IL outputted from the lesion candidate detecting portion 34b, adding the marker image G2 in an appearance DP for emphasizing a position of a lesion candidate area L corresponding to the lesion candidate information IL to the observation image G1. Further, the emphasis processing portion 36a is configured to, after the timing when the continuous detection time period TL reaches the time period TM, cause the appearance of the marker image G2 added to the observation image G1 to differ according to whether detection of the lesion candidate area L by the region of interest detecting portion 34 is successful or not. Further, the emphasis processing portion 36a is configured to, after the timing when the continuous detection time period TL reaches the time period TM, cause the appearance of the marker image G2 added to the observation image G1 to change according to a length of a period during which detection of the lesion candidate area L by the region of interest detecting portion 34 continues. Note that, in the present embodiment, for example, auditory information such as a beep sound or tactile information such as vibration may be caused to change according to the length of the period during which detection of the lesion candidate area L continues.

Note that the emphasis processing portion 36a may perform the emphasis processing using only the position information included in the lesion candidate information IL or using both of the position information and the size information included in the lesion candidate information IL as far as the emphasis processing portion 36a generates the marker image G2 for emphasizing the position of the lesion candidate area L.

The display device 41 is provided with a monitor or the like and is configured to be capable of displaying a display image outputted from the endoscopic image processing device 32 on the display screen.

Next, operation of the present embodiment will be described. Note that, for simplification, a case where one lesion candidate area L1 is included in the observation image G1 will be described below as an example.

After connecting and powering on each portion of the endoscope system 1, a user performs an operation for inserting the insertion portion 22 into an examinee's body cavity.

For example, when the light source driving device 11 and the video processor 31 are powered on, the endoscope 21 radiates illumination light to an object, receives reflected light from the object, picks up an image of the received reflected light to generate an image pickup signal and outputs the generated image pickup signal to the video processor 31.

The video processor 31 generates an observation image G1 of the object by performing the predetermined processing for the image pickup signal outputted from the endoscope 21, and sequentially outputs frames of the generated observation image G1 to the endoscopic image processing device 32, one frame at a time.

The lesion candidate detecting portion 34b detects a lesion candidate area L1 included in the observation image G1, acquires lesion candidate information IL1, which is information showing the detected lesion candidate area L1, and outputs the acquired lesion candidate information IL1 to each of the continuous detection judging portion 35 and the display controlling portion 36.

At a timing when the lesion candidate information IL1 is inputted, that is, at a timing when detection of the lesion candidate area L1 by the region of interest detecting portion 34 is started, the display controlling portion 36 starts measurement of the continuous detection time period TL. The display controlling portion 36 continues measurement of the continuous detection time period TL during a period during which a judgment result that detection of the lesion candidate area L1 in the observation image G1 continues is being inputted. Further, at a timing when input of the judgment result that detection of the lesion candidate area L1 in the observation image G1 continues stops, that is, at a timing when detection of the lesion candidate area L1 by the region of interest detecting portion 34 discontinues, the display controlling portion 36 stops measurement of the continuous detection time period TL.

Figure 3:
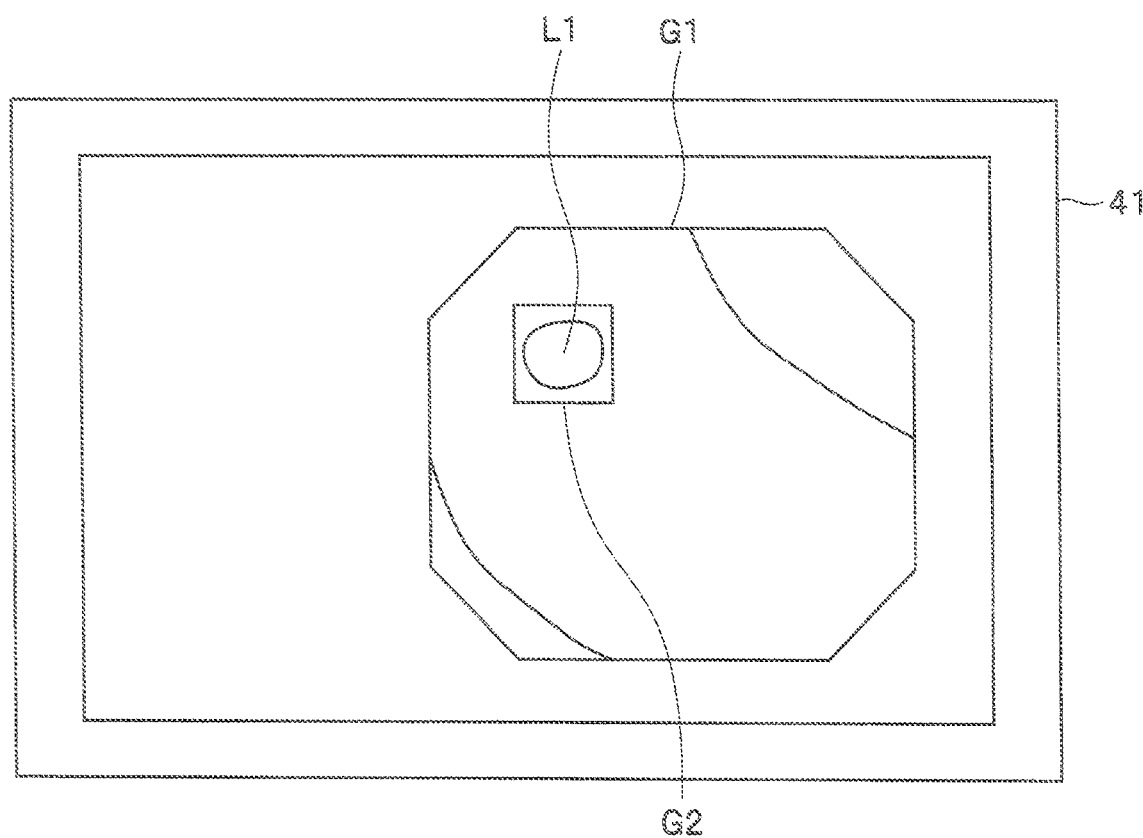
FIG. 3 is a diagram showing an example of a display image displayed on a display device after processing by the endoscopic image processing device according to the embodiment.

At the timing when the continuous detection time period TL reaches the time period TM, the emphasis processing portion 36a starts the emphasis processing by, based on lesion candidate information IL1 outputted from the lesion candidate detecting portion 34b, adding the marker image G2 in the appearance DP for emphasizing a position of the lesion candidate area L1 to the observation image G1. According to such processing by the emphasis processing portion 36a, at the timing when the continuous detection time period TL reaches the time period TM, a solid-line square surrounding the lesion candidate area L1 detected by the lesion candidate detecting portion 34b is added as the marker image G2 in the appearance DP, and the observation image G1 added with the marker image G2 in the appearance DP is displayed on the display device 41 as a display image, for example, as shown in FIG. 3. FIG. 3 is a diagram showing an example of a display image displayed on a display device after processing by the endoscopic image processing device according to the embodiment.

Note that the time period TM is a time period to start the emphasis processing by the emphasis processing portion 36a at the time of measuring the continuous detection time period TL and is set in advance as a time period shorter than a time period TA described later. Therefore, in the present embodiment, when the time period TM elapses after detection of a lesion candidate area L1 by the region of interest detecting portion 34 is started, the emphasis processing by the emphasis processing portion 36a is started.

After the timing when the continuous detection time period TL reaches the time period TM, the emphasis processing portion 36a causes the appearance of the marker image G2 added to the observation G1 to differ according to whether detection of the lesion candidate area L1 by the region of interest detecting portion 34 is successful or not and causes the appearance of the marker image G2 added to the observation image G1 to change according to a length of a period during which detection of the lesion candidate area L1 continues.

Figure 4:
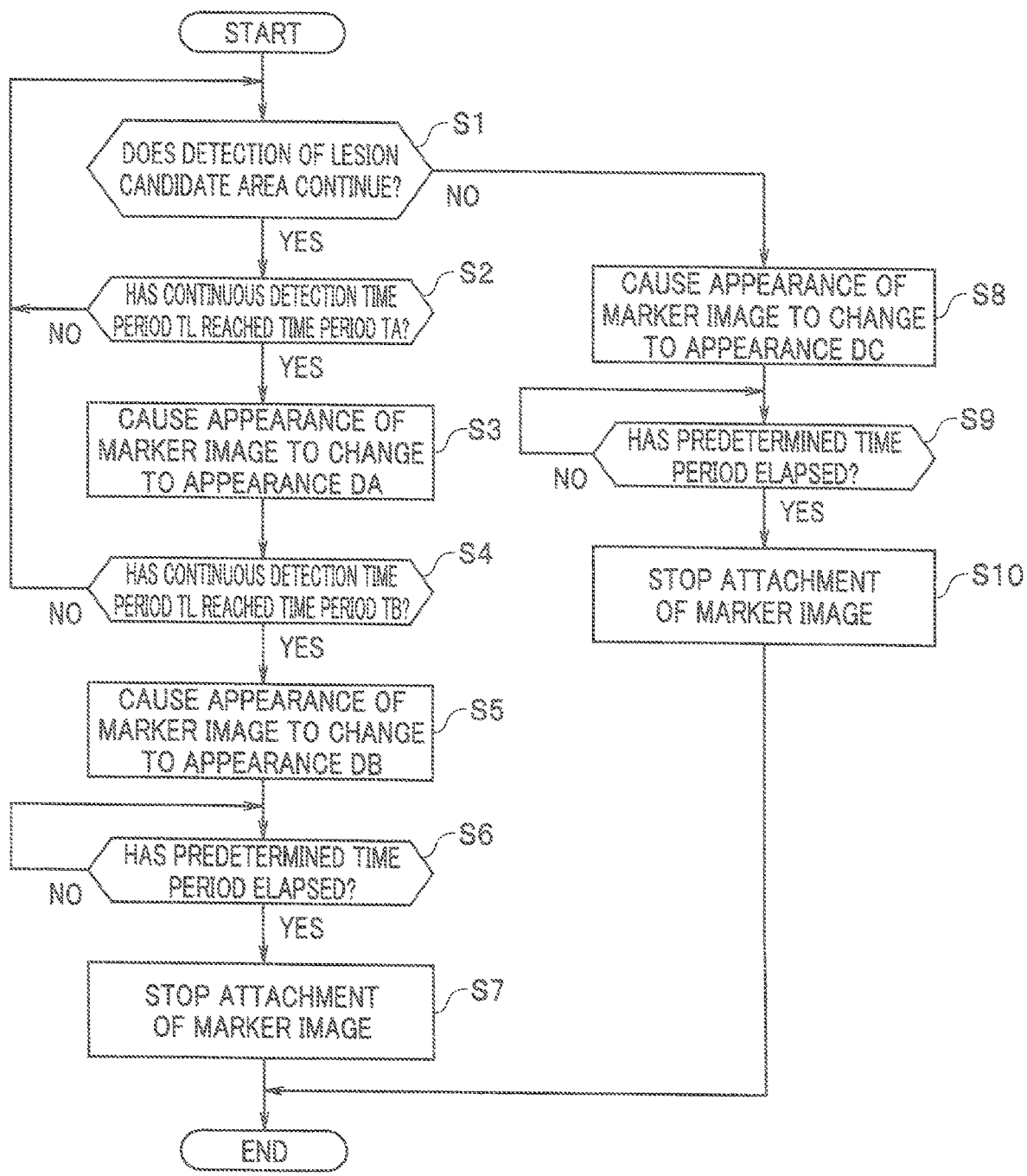
FIG. 4 is a diagram for illustrating an example of the processing performed in the endoscopic image processing device according to the embodiment.

Here, a specific example of the processing performed by the emphasis processing portion 36a of the present embodiment will be described with reference to FIG. 4 and the like. FIG. 4 is a diagram for illustrating an example of the processing performed in the endoscopic image processing device according to the embodiment.

The emphasis processing portion 36a detects whether detection of the lesion candidate area L1 by the region of interest detecting portion 34 continues or not, based on a judgment result outputted from the continuous detection judging portion 35 (step S1 in FIG. 4).

If detecting that detection of the lesion candidate area L1 by the region of interest detecting portion 34 continues (S1: YES), the emphasis processing portion 36a subsequently performs processing of step S2 in FIG. 4 described later. If detecting that detection of the lesion candidate area L1 by the region of interest detecting portion 34 has discontinued (S1: NO), the emphasis processing portion 36a subsequently performs processing of step S8 in FIG. 4 described later.

If detecting that detection of the lesion candidate area L1 by the region of interest detecting portion 34 continues, the emphasis processing portion 36a judges whether or not the continuous detection time period TL has reached the time period TA longer than the time period TM (step S2 in FIG. 4). Note that it is assumed that the time period TA is set in advance, for example, as a time period during which change in the appearance of the marker image G2 by processing of step S3 in FIG. 4 described later can be visually confirmed, before the continuous detection time period TL reaches a time period TB described later after reaching the time period TM. In other words, the time period TA is set in advance as a time period longer than the time period TM and shorter than the time period TB described later.

If detecting that the continuous detection time period TL has not reached the time period TA (S2: NO), the emphasis processing portion 36a performs the processing of step S1 in FIG. 4 again, keeping the appearance of the marker image G2 in the appearance DP. If detecting that the continuous detection time period TL has reached the time period TA (S2: YES), the emphasis processing portion 36a performs processing for causing the appearance of the marker image G2 added to the observation G1 to change from the appearance DP to an appearance DA (step S3 in FIG. 4) and, after that, performs processing of step S4 in FIG. 4 described later.

Figure 5:
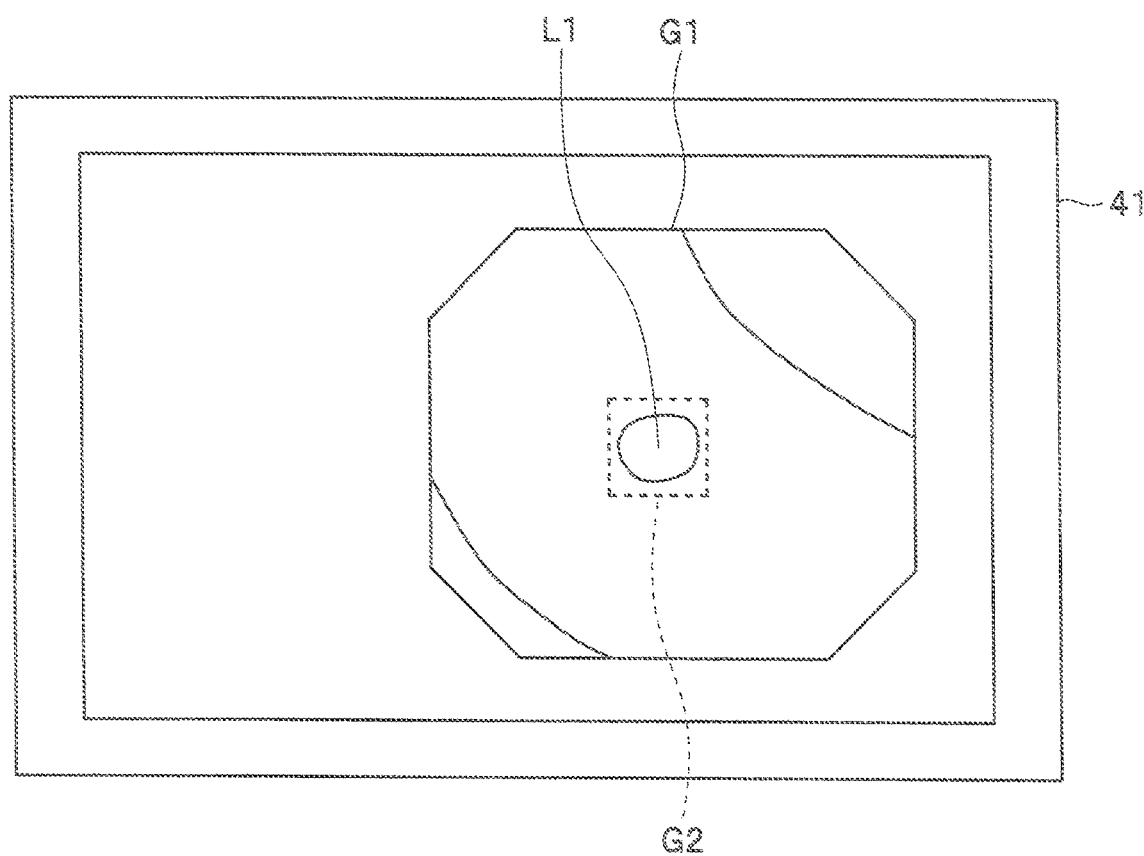
FIG. 5 is a diagram showing an example of the display image displayed on the display device after the processing by the endoscopic image processing device according to the embodiment.

More specifically, if detecting that the continuous detection time period TL has reached the time period TA, the emphasis processing portion 36a performs processing for causing respective sides of the square surrounding the lesion candidate area L1 detected by the lesion candidate detecting portion 34b to change from the solid lines to short-dashed lines to show the short-dashed lines as the marker image G2 added to the observation G1 which is a display image displayed on the display device 41, for example, as shown in FIG. 5. FIG. 5 is a diagram showing an example of the display image displayed on the display device after the processing by the endoscopic image processing device according to the embodiment.

In other words, according to the processing of step S3 in FIG. 4, at the timing when the continuous detection time period TL reaches the time period TA, the marker image G2 in the appearance DA different from the appearance DP is added to the observation image G1.

The emphasis processing portion 36a judges whether or not the continuous detection time period TL has reached the time period TB longer than the time period TA (step S4 in FIG. 4). Note that it is assumed that the time period TB is set in advance, for example, as a time period in which it can be confirmed that the lesion candidate area L1 detected by the region of interest detecting portion 34 is actually a lesion, that is, that detection of the lesion candidate area L1 by the region of interest detecting portion 34 is successful.

If detecting that the continuous detection time period TL has not reached the time period TB (S4: NO), the emphasis processing portion 36a performs the processing from step S1 in FIG. 4 again, keeping the appearance of the marker image G2 in the appearance DA. If detecting that the continuous detection time period TL has reached the time period TB (S4: YES), the emphasis processing portion 36a performs processing for causing the appearance of the marker image G2 added to the observation G1 to change from the appearance DA to an appearance DB (step S5 in FIG. 4) and, after that, subsequently performs processing of step S6 in FIG. 4 described later.

Figure 6:
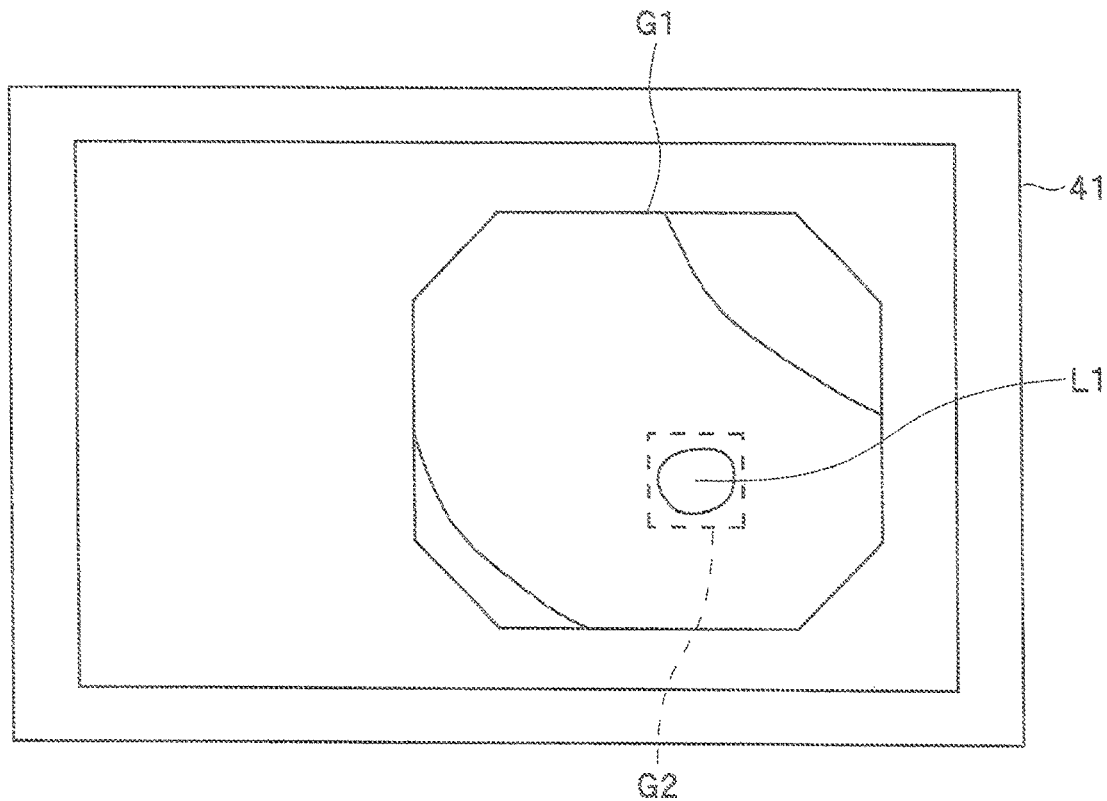
FIG. 6 is a diagram showing an example of the display image displayed on the display device after the processing by the endoscopic image processing device according to the embodiment.

More specifically, if detecting that the continuous detection time period TL has reached the time period TB, the emphasis processing portion 36a performs processing for causing the respective sides of the square surrounding the lesion candidate area L1 detected by the lesion candidate detecting portion 34b to change from the short-dashed lines to long-dashed lines to show the long-dashed lines as the marker image G2 added to the observation G1 which is a display image displayed on the display device 41, for example, as shown in FIG. 6. FIG. 6 is a diagram showing an example of the display image displayed on the display device after the processing by the endoscopic image processing device according to the embodiment.

In other words, according to the processing of step S5 in FIG. 4, at the timing when the continuous detection time period TL reaches the time period TB, the marker image G2 in the appearance DB different from both of the appearances DP and DA is added to the observation image G1.

The emphasis processing portion 36a judges whether or not a predetermined time period has elapsed from a timing immediately after performing the processing of step S5 in FIG. 4 (step S6 in FIG. 4).

Figure 7:
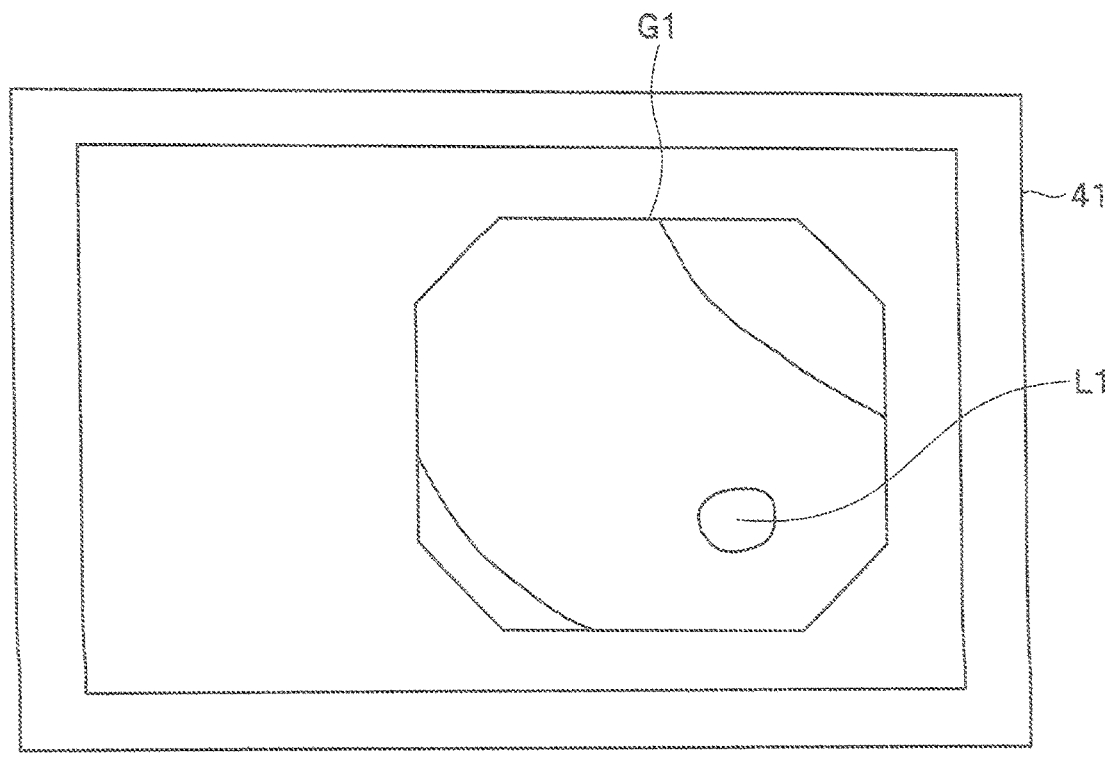
FIG. 7 is a diagram showing an example of the display image displayed on the display device after the processing by the endoscopic image processing device according to the embodiment.

If detecting that the predetermined time period has not elapsed from the timing immediately after performing the processing of step S5 in FIG. 4 (S6: NO), the emphasis processing portion 36a keeps the appearance of the marker image G2 in the appearance DB. If detecting that the predetermined time period has elapsed from the timing immediately after performing the processing of step S5 in FIG. 4 (S6: YES), the emphasis processing portion 36a ends the emphasis processing by stopping addition of the marker image G2 to the observation image G1 (step S7 in FIG. 4). Then, in response to such an operation by the emphasis processing portion 36a, for example, a display image including the observation image G1 as shown in FIG. 7 is displayed on the display device 41. FIG. 7 is a diagram showing an example of the display image displayed on the display device after the processing by the endoscopic image processing device according to the embodiment.

If detecting that detection of the lesion candidate area L1 by the region of interest detecting portion 34 has discontinued before the continuous detection time period TL reaches either the time period TA or TB, the emphasis processing portion 36a performs processing for causing the appearance of the marker image G2 added to the observation image G1 to change from either of the appearance DP or DA to an appearance DC (step S8 in FIG. 4) and, after that, subsequently performs processing of step S9 in FIG. 4 described later.

Figure 8:
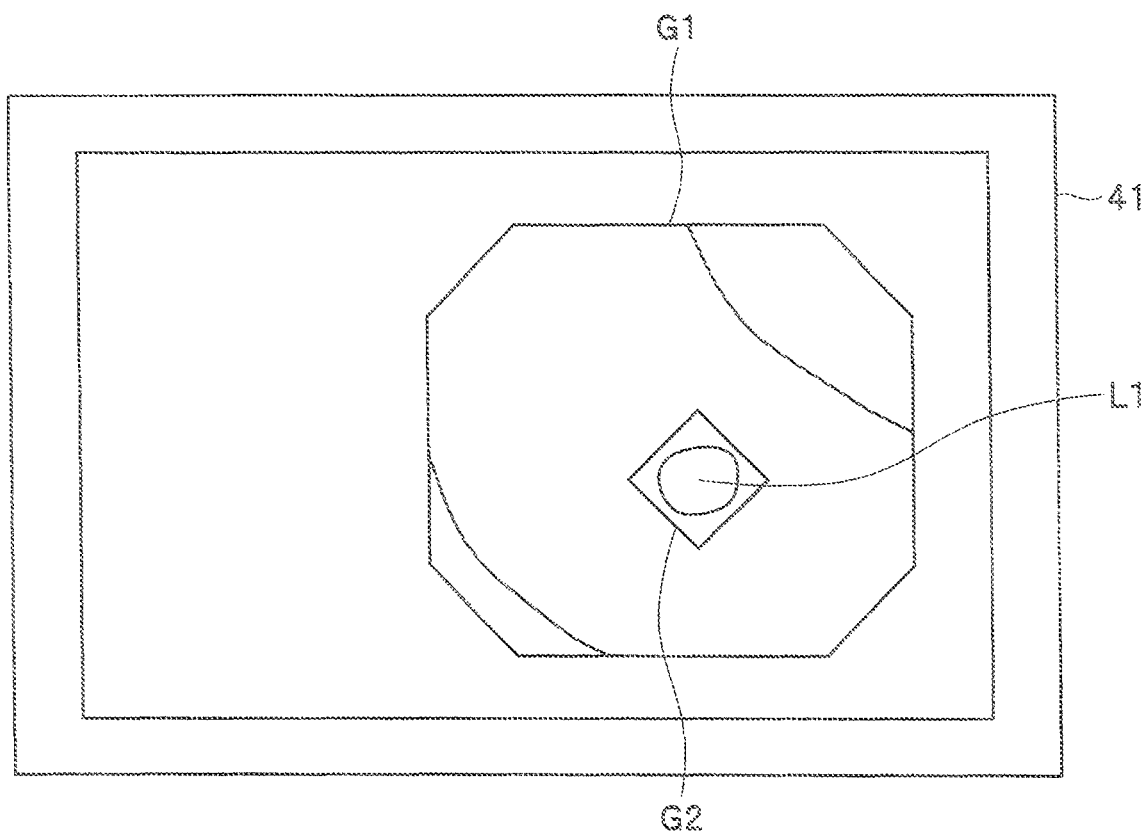
FIG. 8 is a diagram showing an example of the display image displayed on the display device after the processing by the endoscopic image processing device according to the embodiment.

More specifically, if detecting that detection of the lesion candidate area L1 by the region of interest detecting portion 34 has discontinued before the continuous detection time period TL reaches either the time period TA or TB, the emphasis processing portion 36a performs processing for causing a shape of a figure surrounding the lesion candidate area L1 detected by the lesion candidate detecting portion 34b to change from the square to a rhombus, as shown in FIG. 8. FIG. 8 is a diagram showing an example of the display image displayed on the display device after the processing by the endoscopic image processing device according to the embodiment.

In other words, according to the processing of step S8 in FIG. 4, when detection of the lesion candidate area L1 by the region of interest detecting portion 34 discontinues before the continuous detection time period TL reaches either the time period TA or TB, the marker image G2 in the appearance DC different from all of the appearances DP, DA and DB is added to the observation image G1.

The emphasis processing portion 36a judges whether or not a predetermined time period has elapsed from a timing immediately after performing the processing of step S8 in FIG. 4 (step S9 in FIG. 4).

If detecting that the predetermined time period has not elapsed from the timing immediately after performing the processing of step S8 in FIG. 4 (S9: NO), the emphasis processing portion 36a keeps the appearance of the marker image G2 in the appearance DC. If detecting that the predetermined time period has elapsed from the timing immediately after performing the processing of step S8 in FIG. 4 (S9: YES), the emphasis processing portion 36a ends the emphasis processing by stopping addition of the marker image G2 to the observation image G1 (step S10 in FIG. 4). Then, in response to such an operation by the emphasis processing portion 36a, for example, the display image including the observation image G1 as shown in FIG. 7 is displayed on the display device 41.

As described above, according to the series of processing in FIG. 4, for example, if the lesion candidate area L1 detected by the region of interest detecting portion 34 is actually a lesion, the appearance of the marker image G2 added to the observation image G1 changes in order of DP, DA and DB. Further, as described above, according the series of processing in FIG. 4, for example, if the lesion candidate area L1 detected by the region of interest detecting portion 34 is different from a lesion, the appearance of the marker image G2 added to the observation image G1 changes from either DP or DA, to DC. In other words, according to the series of processing in FIG. 4, the emphasis processing portion 36a causes the appearance of the marker image G2 added to the observation image G1 to differ between a case where detection of the lesion candidate area L1 by the region of interest detecting portion 34 continues longer than the time period TB and a case where detection of the lesion candidate area L1 discontinues in a time period shorter than the time period TB, based on a judgment result outputted from the continuous detection judging portion 35. Further, according to the series of processing in FIG. 4, it is possible to cause the appearance of the marker image G2 added to the observation image G1 to differ according to whether detection of the lesion candidate area L1 by the region of interest detecting portion 34 is successful or not, and it is also possible to cause the appearance of the marker image G2 to change according to the length of the period during which detection of the lesion candidate area L1 continues. Therefore, according to the present embodiment, it is possible to present visual information that can be used to judge whether detection of a region of interest such as a lesion is successful or not, and, as a result, it is possible to reduce a burden on a surgeon who visually confirms the region of interest.

Note that, in the present embodiment, the emphasis processing portion 36a may cause an element other than the shape of the marker image G2 to differ according to whether detection of the lesion candidate area L by the region of interest detecting portion 34 is successful or not. More specifically, the emphasis processing portion 36a may cause, for example, a color and/or a pattern of the marker image G2 to differ according to whether detection of the lesion candidate area L by the region of interest detecting portion 34 is successful or not.

Further, in the present embodiment, the time periods TA and TB are not limited to being set as time periods corresponding to the continuous detection time period TL but may be set, for example, as elapsed time periods from the timing when the emphasis processing by the emphasis processing portion 36a is started.

Further, in the present embodiment, the time periods TA and TB are not limited to being set as time periods corresponding to the continuous detection time period TL but may be set, for example, as elapsed time periods from a timing when a lesion candidate area L appears in the observation image G1 if the timing can be estimated based on lesion candidate information IL and the like outputted from the lesion candidate detecting portion 34b.

Note that the present invention is not limited to the above embodiment, and it is, of course, possible to make various changes and applications within a range not departing from the gist of the invention.

What is claimed is:

1. An endoscopic image processing device comprising at least one processor, the at least one processor being configured to perform:
   detecting a region of interest in an observation image, the observation image being obtained by picking up an image of an object and being sequentially input to the at least one processor;
   judging whether or not detection of the region of interest continues, to acquire a judgment result; and
   adding visual information for emphasizing a position of the region of interest to the observation image during a period during which the region of interest is detected,
   wherein the at least one processor performs control to cause an appearance of the visual information added to the observation image to differ between (i) a first case in which the region of interest is continuously detected for at least a predetermined time period and (ii) a second case in which the detection of the region of interest discontinues after being continuously detected for a time period shorter than the predetermined time period, based on the judgment result, and
   wherein the at least one processor performs control to cause the appearance of the visual information to change from a predetermined appearance to a first appearance when an elapsed time period after the detection of the region of interest is started reaches a first time period shorter than the predetermined time period, and to cause the appearance of the visual information to change from the first appearance to a second appearance when the elapsed time period reaches the predetermined time period.

2. The endoscopic image processing device according to claim 1, wherein the at least one processor performs control to cause the appearance of the visual information to change to a third appearance when the detection of the region of interest discontinues before the elapsed time period reaches either the first time period or the predetermined time period, the third appearance being different from all of the predetermined appearance, the first appearance, and the second appearance.

3. The endoscopic image processing device according to claim 1, wherein the at least one processor performs control to stop addition of the visual information to the observation image when a second predetermined time period elapses after the appearance of the visual information is caused to change to the second appearance.

4. The endoscopic image processing device according to claim 2, wherein the at least one processor performs control to stop addition of the visual information to the observation image when a second predetermined time period elapses after the appearance of the visual information is caused to change to the third appearance.

5. The endoscopic image processing device according to claim 1, wherein the at least one processor performs control to start adding the visual information having the predetermined appearance to the observation image when the elapsed time period reaches a second time period shorter than the first time period.

6. The endoscopic image processing device according to claim 1, wherein the at least one processor performs control to cause the visual information to have a third appearance different from the second appearance when the detection of the region of interest discontinues before the elapsed time period reaches the predetermined time period.

7. An endoscopic image processing method comprising:
   detecting a region of interest in an observation image, the observation image being obtained by sequentially picking up images of an object;
   judging whether or not detection of the region of interest continues, to acquire a judgment result;
   adding visual information for emphasizing a position of the region of interest to the observation image during a period during which the region of interest is detected; and
   controlling an appearance of the visual information added to the observation image so as to cause the appearance of the visual information to differ between (i) a first case in which the region of interest is continuously detected for at least a predetermined time period and (ii) a second case in which the detection of the region of interest discontinues after being continuously detected for a time period shorter than the predetermined time period, based on the judgment result,
   wherein the controlling comprises causing the appearance of the visual information to change from a predetermined appearance to a first appearance when an elapsed time period after the detection of the region of interest is started reaches a first time period shorter than the predetermined time period, and causing the appearance of the visual information to change from the first appearance to a second appearance when the elapsed time period reaches the predetermined time period.

* * * * *